United States Patent [19]
Himmele et al.

[11] Patent Number: 4,585,594
[45] Date of Patent: Apr. 29, 1986

[54] PREPARATION OF 4-SUBSTITUTED BUT-3-ENE-1-CARBOXYLIC ACIDS AND THEIR ESTERS

[75] Inventors: Walter Himmele, Walldorf; Werner Hoffmann, Neuhofen; Lothar Janitschke, Kleinniedesheim, all of Fed. Rep. of Germany

[73] Assignee: BASF Aktiengesellschaft, Ludwigshafen, Fed. Rep. of Germany

[21] Appl. No.: 680,514

[22] Filed: Dec. 11, 1984

[51] Int. Cl.$^4$ .................. C07C 51/14; C07C 67/36
[52] U.S. Cl. .................. 260/410.9 R; 260/413; 560/8; 560/55; 560/101; 560/104; 560/114; 560/207; 562/406; 562/465; 562/491; 562/495; 562/517; 549/323; 549/427
[58] Field of Search .................. 560/207, 214, 8, 55, 560/101, 104; 562/406, 465, 491, 495, 517; 260/410.9 M, 410.9 N, 413 R; 549/323, 427

[56] References Cited
PUBLICATIONS

Tsuji et al., in J. Am. Chem. Soc. 86 (1964), pp. 4350–4353.
Bittler et al., Angew. Chemie, 80 (1968), pp. 352–359.

Primary Examiner—Natalie Trousof
Assistant Examiner—L. Hendriksen
Attorney, Agent, or Firm—John H. Shurtleff

[57] ABSTRACT

4-Substituted but-3-ene-1-carboxylic acids and their esters $R^1R^2C=CH-CH_2-CO-O-R^3$ (I, where $R^1$ is an organic radical, $R^2$ is H or $R^1$, or $R^1$ and $R^2$ together form a 5-membered to 20-membered ring, and $R^3$ is H or lower alkyl) are prepared by carbonylation of $R^1R^2C(OH)-CH=CH_2$ (II) in the presence of an alcohol $R^{3'}-OH$ (III, where $R^{3'}$ is lower alkyl) or, for the preparation of the acids I alone, in the absence of an alcohol III, at from 50° to 150° C. and under from 200 to 700 bar, using a complex of a palladium halide and a tertiary organic phosphine.

6 Claims, No Drawings

PREPARATION OF 4-SUBSTITUTED BUT-3-ENE-1-CARBOXYLIC ACIDS AND THEIR ESTERS

The present invention relates to a novel process for the preparation of 4-substituted but-3-ene-1-carboxylic acids or their esters of the general formula I

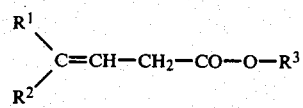
(I)

where $R^1$ is an organic radical, $R^2$ is hydrogen or an organic radical, and $R^1$ and $R^2$ may furthermore be bonded to one another to form a 5-membered to 20-membered ring and should be inert under the reaction conditions described below, and $R^3$ is hydrogen or lower alkyl.

Tsuji et al., in J. Am. Chem. Soc. 86 (1964), 4350–4353, disclose that ethyl pent-3-ene-1-carboxylate (I, where $R^1$ is Me, $R^2$ is H and $R^3$ is Et) can be prepared by carbonylation of but-1-en-3-ol with carbon monoxide and ethanol in the presence of palladium chloride as a carbonylation catalyst. However, the yield of only 39% achieved in this procedure is unsatisfactory for industrial purposes.

Furthermore, Bittler et al., in Angew. Chemie, 80 (1968), 352–359, disclose that allyl alcohol and methanol can be carbonylated using a palladium chloride/triphenylphosphine complex to give methyl but-3-enecarboxylate in 65% yield. According to the authors (cf. loc cit, page 355), the carbonylation of the allyl alcohol takes place with retention of the double bond, so that the 4-substituted but-3-enecarboxylates have to be prepared using, as starting materials, the allyl alcohols

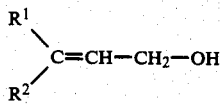

which are difficult to obtain.

It is an object of the present invention to make the compounds I more readily accessible, these compounds generally being important for organic syntheses, and some of them being directly useful as fragrance materials.

We have found, unexpectedly in view of the work by Bittler et al., that this object is achieved by a process for the preparation of the compounds (I) defined at the outset, by carbonylation of a derivative of allyl alcohol with the aid of a palladium halide, wherein an allyl alcohol II

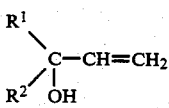
(II)

is carbonylated with carbon monoxide at 50°–150° C. and under 200–700 bar,
(a) together with an alcohol III

  R³′—OH (III)

where $R^{3'}$ is lower alkyl, if a predominant amount of an ester I is to be prepared, or (b) without a further reactant where an acid I is to be prepared, in the presence of an effective amount of a complex of a palladium halide and a tertiary phosphine (IV).

The starting compounds II are obtainable in a simple manner from the corresponding carbonyl compounds $R^1$—CO—$R^2$ and vinyl magnesium halides. II can also be prepared from the carbonyl compounds and acetylides, such as sodium acetylide, with subsequent partial hydrogenation of the ethynyl group to the vinyl group.

On the basis of the very extensive investigations carried out to date, the nature of the compounds II, ie. the type of organic radicals $R^1$ and $R^2$, is in principle unimportant with regard to the novel process, provided that these radicals do not contain any substituents or groups which are reactive under the carbonylation conditions. Examples of such reactive radicals are alkenyl groups having terminal double bonds; if, on the other hand, the double bond is an internal one, it is as a rule virtually never attacked under the reaction conditions.

Examples of suitable radicals $R^1$ and $R^2$ are aliphatic radicals of 1 to 30 carbon atoms, cycloaliphatic radicals having 3 to 12 ring members, aromatic radicals possessing from 1 to 3 isocyclic or heterocyclic aromatic rings, mixed radicals containing aliphatic and/or cycloaliphatic and/or aromatic groups in any sequence, and cyclic radicals which have from 3 to 20 ring members, are formed by $R^1$ and $R^2$ together and can in turn be substituted by the above radicals.

All of these radicals can furthermore contain substituents such as halogen, eg. fluorine or chlorine, hydroxyl (which in general is virtually never attacked during the carbonylation according to the invention), substituted amino, cyano, nitro, alkoxy, acyl, acyloxy, carbalkoxy, thiol, mercaptan, carboxamide or alkylsulfonyl. Particularly important alcohols II are those whose molecule contains one or more isoprene skeletons; the compounds I derived from these are often typical fragrance materials.

Suitable alcohols III are mainly lower alcohols, such as methanol and ethanol, since the carbonylation proceeds most rapidly with these. Higher alcohols of not more than about 6 carbon atoms can in principle also be used, although it is frequently more advantageous to introduce these into the molecule by transesterification of the methyl or ethyl esters I.

In general, it is preferable to use a molar excess of the alcohol III over the alcohol II. Usually, the molar ratio of III to II is from 2:1 to 6:1. If III is used as a solvent, this ratio may also be higher.

If the procedure is carried out in the absence of a further reactant, ie. without an alcohol III, the acids I are obtained. Predominant amounts of acid are also generally obtained when a tertiary alcohol III, eg. tert.-butanol, is used.

The carbonylation catalysts are complexes of a palladium halide, eg. the bromide or in particular the chloride, and a tertiary organic phosphine (IV). Since formation of these complexes takes place directly under the reaction conditions, the said complexes are advantageously employed in the form of their components; however, it is of course also possible to start from the preprepared complexes, eg. Pd(PPh₃)₂Cl₂ (Ph=phenyl).

The tertiary phosphines IV are of the general formula IV

where $R^4$, $R^5$ and $R^6$ are each an organic radical.

In particular, $R^4$, $R^5$ and $R^6$ can each be alkyl of 4 to 18 carbon atoms, $C_1$-$C_4$-alkylphenyl or, especially, phenyl. Two of these radicals may furthermore be bonded to one another to form a 5-membered to 8-membered ring, and it is of course also possible to use compounds possessing 2 or more tertiary phosphine groups, eg. 1,2-bis-(diphenylphosphino)-ethane.

The type of phosphines is in principle unimportant, so that it is in general preferable to use the cheapest member of this class of substances, ie. triphenylphosphine.

It is also advantageous to carry out the reaction in the presence of free phosphine, ie. phosphine which is not bonded in a complex. The preferred molar ratio of phosphine to Pd is from 3:1 to 10:1.

It is not possible to state a particular value for the effective amount of the catalyst because the reaction takes place in principle with infinitely small amounts of Pd, but is of course then very slow, and because large amounts have no adverse effect. Hence, the amount of Pd depends on the reactivity of the alcohol II and on the reaction time desired. In general, the amount of Pd is from 0.1 to 5 g per mole of II.

According to the general principles of process engineering, the reaction takes place most readily and most rapidly in the substantially homogeneous liquid phase. In general, homogeneity results automatically under the reaction conditions owing to the presence of the alcohol III, so that an additional solvent need not be used. If, however, the alcohol II is sparingly soluble, it is advisable to use a solvent, such as toluene, diethyl ether or tetrahydrofuran.

The pressure, which for the most part corresponds to the CO partial pressure, is in general from 100 to 650, in particular from 300 to 600, bar, and the recommended temperature is from 50° to 150° C., preferably from 90° to 110° C. Under these conditions, and using the recommended amounts of catalyst, the reaction times are about 1–24 hours.

The novel process can be carried out continuously or batchwise, and the method used is identical to the conventional carbonylation technique, so that more detailed description of this can be dispensed with. The same applies to the working up of the reaction mixtures. Owing to the sensitivity of the phosphines to oxidation, it is advisable to carry out the procedure in the absence of atmospheric oxygen.

When the alcohol III is also used, the products obtained are mainly the esters I, the free acids 1 also resulting; tertiary alcohols III generally give larger amounts of the acid. The amount of by-products is low in every case, although it was expected that the alcohols II would be dehydrated under the reaction conditions. The compounds I can be formed in the cis or trans form, predominant amounts of the trans isomer usually being obtained.

EXAMPLES

Various alcohols II were reacted with various alcohols III, in each case in the absence of atmospheric oxygen, at 100° C., in the presence of palladium chloride and triphenylphosphine ($Pph_3$), to give the acids or esters I.

Details of the other reaction conditions and of the results of the experiments are shown in the Table below. About 98% of the stated pressure is due to the CO partial pressure. Each of the reactions was terminated when scarcely any further CO was consumed.

The products were identified by means of gas chromatographic, H—NMR, $^{13}C$—NMR, mass spectroscopic and IR analysis. The yields were determined gravimetrically; where separation into the acid and the ester presented difficulties, only the sum of the yields was determined. Boiling points and melting points are stated wherever they were obtained directly from the experiments.

| Example | Alcohol II [g] | Alcohol III [g] | $PdCl_2$ [g] $PPh_3$ [g] | Pressure [bar] | Duration [h] | Yields acid/ester I Total yield, trans/cis ratio q Characteristics |
|---|---|---|---|---|---|---|
| 1 | Pent-1-en-3-ol 100 | MeOH 50 | 1.0 3.0 | 600 | 17 | 14% hex-3-enoic acid<br>_78%_ methyl hex-3-enoate, bp. 100–101° C./<br>92% q = 85:15 231 mbar |
| 2 | Hex-1-en-3-ol 100 | EtOH 50 | 1.0 3.0 | 600 | 8 | 15% hept-3-enoic acid<br>_54%_ ethyl hept-3-enoate, bp. 89° C./45 mbar<br>69% q = 85:15<br>scent, acid: greenish, fruity, somewhat pungent<br>ester: sweetish, floral, somewhat tonka-like |
| 3 | Hept-1-en-3-ol 920 | EtOH 500 | 5.0 1.5 | 300 | 15 | 18% oct-3-enoic acid<br>_69%_ ethyl oct-3-enoate, bp. 112–114° C./<br>87% q = 80:20 54 mbar<br>scent, acid and ester: greenish, slightly fatty |
| 4 | Oct-1-en-3-ol 730 | n-propanol 500 | 5.0 15.0 | 300 | 8 | 15% non-3-enoic acid<br>_64%_ n-propyl non-3-enoate, bp. 70–72° C./<br>79% q = 82:18 4 mbar<br>scent, ester: green, slightly herbaceous, fungal |
| 5 | 3-Methylbut-1-en-3-ol 1,000 | MeOH 500 | 2.5 7.5 | 300 | 8 | 9% 4-methylpent-3-enoic acid, bp. 122° C./<br>_47%_ 48 mbar<br>56% methyl 4-methylpent-3-enoate, bp. 110° C./150 mbar |
| 6 | 3,7-Dimethyloct-1-en-3-ol 1,000 | i-propanol 500 | 2.5 7.5 | 300 | 8 | 23% 4,8-dimethylnon-3-enoic acid,<br>_57%_ bp. 165° C./45 mbar |

-continued

| Example | Alcohol II [g] | Alcohol III [g] | PdCl$_2$ [g] PPh$_3$ [g] | Pressure [bar] | Duration [h] | Yields acid/ester I Total yield, trans/cis ratio q Characteristics |
|---|---|---|---|---|---|---|
| | | | | | | 80% isopropyl 4,8-dimethylnon-3-enoate, bp. 145° C./37 mbar q = 87:13 |
| 7 | 3,7-Dimethyloct-1-en-3-ol 1,000 | n-propanol 500 | 5 15 | 300 | 8 | 13% 4,8-Dimethylnon-3-enoic acid 68% n-propyl 4,8-dimethylnon-3-enoate, 81% bp. 147° C./34 mbar cis-ester: sweetish, balsamic, fruity trans-ester: floral, somewhat fatty |
| 8 | 3,7-Dimethyloct-1-en-3-ol 1,000 | n-butanol 5,000 | 5 15 | 300 | 15 | 17% 4,8-dimethylnon-3-enoic acid 63% n-butyl 4,8-dimethylnon-3-enoate, 80% bp. 160° C./37 mbar q = 66:34 |
| 9 | 3,7-Dimethylocta-1,6-dien-3-ol 1,000 | EtOH 500 | 5 15 | 250 | 14 | 22% 4,8-dimethylnona-3,7-dienoic acid 61% ethyl 4,8-dimethylnona-3,7-dienoate 83% bp. 82–84° C./4 mbar q = 68:32 cis-ester: fruity, greenish trans-ester: pleasantly fruity, musk-like |
| 10 | 3,7-Dimethylocta-1,6-dien-3-ol 1,000 | EtOH 500 | 2.5 7.5 | 300 | 10 | 34% 4,8-dimethylnona-3,7-dienoic acid 56% ethyl 4,8-dimethylnona-3,7-dienoate 90% bp. 82° C./4 mbar |
| 11 | 3,7,11-Trimethyldodec-1-en-3-ol 410 | EtOH 205 | 2.5 7.5 | 300 | 6 | 3% 4,8,12-trimethyltridec-3-enoic acid 90% ethyl 4,8,12-trimethyltridec-3-enoate 93% bp. 125–130° C./4 mbar q = 80:20 |
| 12 | 3,7,11-Trimethyldodeca-1,6-dien-3-ol (dihydronerolidol) 1,125 | MeOH 500 | 2.5 7.5 | 300 | 6 | 11% 4,8,12-trimethyltrideca-3,7-dienoic acid 63% 74% methyl 4,8,12-trimethyltrideca-3,7-dienoate, bp. 125–129° C./4 mbar |
| 13 | 3,7,11-Trimethyl-dodeca-1,6-dien-3-ol (dihydronerolidol) 1,000 | EtOH 500 | 5 15 | 300 | 8 | 6% 4,8,12-trimethyltrideca-3,7-dienoic acid 81% 87% ethyl 4,8,12-trimethyltrideca-3,7-dienoate |
| 14 | 3,7,11-Trimethyl-dodeca-1,6,10-trien-3-ol (nerolidol) 1,000 | MeOH 500 | 2.5 7.5 | 300 | 10 | 7% 4,8,12-trimethyltrideca-3,7,11-trienoic acid 79% 86% methyl 4,8,12-trimethyltrideca-3,7,11-trienoate, bp. 129–130° C./4 mbar |
| 15 | 3,7,11-Trimethyl-dodeca-1,6,10-trien-3-ol (nerolidol) 1,000 | EtOH 500 | 2.5 7.5 | 300 | 14 | 7% 4,8,12-trimethyltrideca-3,7,11-trienoic acid 79% 86% ethyl 4,8,12-trimethyltrideca-3,7,11-trienoate, bp. 126–130° C./4 mbar |
| 16 | 3,7,11-Trimethyl-dodeca-1,6,10-trien-3-ol (nerolidol) 1,000 | EtOH 500 | 1.25 3.75 | 300 | 17 | 9% 4,8,12-trimethyltrideca-3,7,11-trienoic acid 69% 77% ethyl 4,8,12-trimethyltrideca-3,7,11-trienoate, bp. 127–152° C./4 mbar |
| 17 | 3,7,11,15-Tetramethyl-hexadec-1-en-3-ol (isophytol) 1,000 | EtOH 500 | 2.5 7.5 | 300 | 19 | 4% 4,8,12,16-tetramethylheptadec-3-enoic acid 90% 94% ethyl 4,8,12,16-tetramethylheptadec-3-enoate, bp. 162–167° C./4 mbar q = 3:1 |
| 18 | 5-(2,6,6-Trimethylcyclo-hex-1-en-1-yl)-3-methyl-pent-1-en-3-ol 600 | EtOH 300 | 3.5 10.0 | 300 | 4 | 8% 6-(2,6,6-trimethylcyclohex-1-yl)-4-methylhex-3-enoic acid 76% ethyl 6-(2,6,6-trimethylcyclohex-1-yl)-4-methylhex-3-enoate, 84% bp. 148–157° C./5 mbar q = 82:18 cis-ester: sweet fruity (apple, strawberry) |
| 19 | 5-(2,6,6-Trimethylcyclo-hex-1-en-1-yl)-3-methyl-penta-1,4-dien-3-ol (vinylionol) 100 | EtOH 50 | 1.0 3.0 | 600 | 10 | * 6-(2,6,6-trimethylcyclohex-1-enyl)-4-methylhexa-3,5-dienoic acid ethyl 6-(2,6,6-trimethylcyclohex-1-enyl)-4-methylhexa-3,5-dienoate, bp. 159–162° C. 25% mixture: fruity, damsony apricot |
| 20 | 3-Ethylpent-1-en-3-ol 120 | EtOH 60 | 1.0 3.0 | 600 | 22 | 11% 4-ethylpent-3-enoic acid 54% ethyl 4-ethylpent-3-enoate, bp. 106–107° C./52 mbar 65% ester: pungent, greenish, fruity |
| 21 | 4-Vinylheptan-4-ol 100 | EtOH 50 | 1.0 3.0 | 600 | 17 | 6% 4-n-propylhept-3-enoic acid 56% ethyl 4-n-propylhept-3-enoate, bp. 53–55° C./4 mbar 62% ester: fruity, green, rubbery |
| 22 | 1-Vinylcyclododecan-1-ol 100 | EtOH 50 | 1.0 3.0 | 600 | 23 | 8% 3-(cyclododecylidene)-propionic acid 61% ethyl 3-(cyclododecylidene)-propion- |

-continued

| Example | Alcohol II [g] | Alcohol III [g] | PdCl₂ [g] PPh₃ [g] | Pressure [bar] | Duration [h] | Yields acid/ester I Total yield, trans/cis ratio q Characteristics |
|---|---|---|---|---|---|---|
| 23 | 2-Methyl-1-vinyl-cyclohexan-1-ol 93.5 | EtOH 46.7 | 1.0 3.0 | 600 | 17 | 69% ate, bp. 144–146° C./4 mbar ester: fatty, tart, slightly sweetish, balsamic<br>5% 3-(2-methylcyclohexylidene)-propionic acid<br>51% ethyl 3-(2-methylcyclohexylidene)-propionate, bp. 116–122° C./28 mbar |
| 24 | 3-Methyl-1-vinyl-cyclohexan-1-ol 92 | EtOH 46 | 1.0 3.0 | 600 | 34 | 56%<br>5% 3-(3-methylcyclohexylidene)-propionic acid<br>73% ethyl 3-(3-methylcyclohexylidene)-propionate, bp. 105–110° C./16 mbar<br>78% ester: fruity, sweetish, fatty alcohol-like |
| 25 | 1-Vinyl-cyclohexan-1-ol 876 | EtOH 500 | 2.5 7.5 | 300 | 17 | 12% 3-(cyclohexylidene)-propionic acid<br>58% ethyl 3-(cyclohexylidene)-propionate<br>70% bp. 130° C./30 mbar ester: fruity, strawberry-like, tart |
| 26 | 3,3-Dimethyl-1-vinyl-cyclohexan-1-ol 90 | EtOH 50 | 1.0 3.0 | 600 | 7 | 3% 3-(3,3-dimethylcyclohexylidene)-propionic acid,<br>76% ethyl 3-(3,3-dimethylcyclohexylidene)-propionate, bp. 138–140° C./40 mbar<br>79% q = 50:50 ester: woody, fruity, greenish |
| 27 | Mixture of 2,2,4- and 2,4,4-trimethyl-1-vinyl-cyclopentan-1-ol 100 | EtOH 50 | 1.0 3.0 | 600 | 16 | 4% 3-(2,2,4/2,4,4-trimethylcyclopentylidene)-propionic acid<br>58% ethyl 3-(2,2,4/2,4,4-trimethylcyclopentylidene)-propionate, bp. 62–63° C./4 mbar<br>62% ester: green, earthy, fungal, woody |
| 28 | 1-Vinyl-1-hydroxy-1,2,3,4-tetrahydronaphthalene 100 | EtOH 100 | 1.0 3.0 | 600 | 13 | 5% 2,3-benzocyclohexylid-1-enepropionic acid<br>60% ethyl 2,3-benzocyclohexylid-1-ene-propionate, bp. 110° C./4 mbar<br>65% q = 70:30 |
| 29 | 9-Vinyl-9-hydroxyfluorene 85 | EtOH 50 | 1.0 3.0 | 600 | 10 | <1% 3-(fluorenylid-9-ene)-propionic acid<br>83% ethyl 3-(fluorenylid-9-ene)-propionate, bp. 60–65° C.<br>83% |
| 30 | 3,3-Diphenylprop-1-en-3-ol 73 | EtOH 50 | 1.0 3.0 | 600 | 10 | 8% 4,4-diphenylbut-3-enoic acid<br>72% ethyl 4,4-diphenylbut-3-enoate,<br>80% bp. 168° C./4 mbar |
| 31 | 3-Phenylbut-1-en-3-ol 70 | EtOH 50 | 1.0 3.0 | 600 | 8 | 5% 4-phenyl-but-3-enoic acid<br>40% ethyl 4-phenyl-but-3-enoate bp. 159° C./40 mbar<br>30% 2-methyl-2-phenylbutyrolactone,<br>75% bp. 165–167° C./40 mbar |
| 32 | 3-(3,3-Dimethylcyclohex-1-yl)-but-1-ene 100 | EtOH 50 | 1.0 3.0 | 600 | 5 | 8% 4-(3,3-dimethylcyclohex-1-yl)-pent-3-enoic acid<br>65% ethyl 4-(3,3-dimethylcyclohex-1-yl)-pent-3-enoate, bp. 80–82° C./4 mbar<br>73% q = 1:1 |
| 33 | 3-Cyclopropylbut-1-en-3-ol 100 | EtOH 50 | 1.0 3.0 | 600 | 15 | 4% 4-cyclopropylbut-3-enoic acid<br>38% ethyl 4-cyclopropylbut-3-enoate, bp. 113–115° C./44 mbar<br>42% |
| 34 | 3-Methoxybut-1-en-3-ol 80 | EtOH 50 | 1.0 3.0 | 530 | 12 | 4% 4-methoxypent-3-enoic acid<br>38% ethyl 4-methoxypent-3-enoate, bp. 117–125° C./74 mbar<br>42% q = 80:20 |
| 35 | 3-Methyl-4-phenyl-but-1-en-3-ol 101 | EtOH 50 | 1 3 | 680 | 20 | 12% 4-methyl-5-phenyl-but-3-enoic acid<br>68% ethyl 4-methyl-5-phenyl-but-3-enoate, bp. 98–99° C./4 mbar<br>80% q = 65:35 ester: green, pelargonium leaves |
| 36 | 1-Vinyl-cycloheptan-1-ol 105 | EtOH 45 | 1 3 | 600 | 13 | 11% 3-cycloheptylidene-propionic acid<br>58% ethyl 3-cycloheptylidene-propionate<br>69% bp. 132° C./24 mbar |
| 37 | 3-(4-Methoxyphenyl)-but-1-en-3-ol 100 | EtOH 50 | 1 3 | 300 | 16 | 2% 4-(4-methoxyphenyl)-pent-3-enoic acid<br>40% ethyl 4-(4-methoxyphenyl)-pent-3-enoate, bp. 157–159° C./40 mbar<br>33% 5-(4-methoxyphenylmethyl)-butyrolactone, bp. 165–167° C./40 mbar<br>75% |
| 38 | 4-tert.-Butoxy-hex-1-en-3-ol 58 | EtOH 50 | 0.5 1.5 | 300 | 11 | 11% 5-tert.-butoxy-hept-3-enoic acid<br>52% ethyl 5-tert.-butoxy-hept-3-enoate, bp. 85–86° C./4 mbar<br>63% |
| 39 | 3-(2-Methoxyphenyl)-but-1-en-3-ol 37 | EtOH 50 | 0.5 1.5 | 300 | 26 | 8% 4-(2-methoxyphenyl)-pent-3-enoic acid<br>72% ethyl 4-(2-methoxyphenyl)-pent-3-enoate, bp. 122–128° C./4 mbar<br>80% |

-continued

| Example | Alcohol II [g] | Alcohol III [g] | PdCl$_2$ [g] PPh$_3$ [g] | Pressure [bar] | Duration [h] | Yields acid/ester I Total yield, trans/cis ratio q Characteristics |
|---|---|---|---|---|---|---|
| 40 | 2-Benzyl-1-vinyl-cyclo-hexan-1-ol 37 | EtOH 37 | 1 3 | 600 | 26 | 4% 3-(2-benzylcyclohexylidene)-propionic acid <br> 79% ethyl 3-(2-benzylcyclohexylidene)-propionate, bp. 163–182° C./4 mbar |
| 41 | 3-(Tetrahydropyran-3-yl)-prop-1-en-3-ol 100 | EtOH 50 | 1 3 | 650 | 13 | 83% <br> 11% 4-(tetrahydropyran-3-yl)-but-3-enoic acid <br> 66% ethyl 4-(tetrahydropyran-3-yl)-but-3-enoate, bp. 72–74° C./4 mbar <br> 77% q = 90:10 |
| 42 | Bis-(4-chlorophenyl)-vinylcarbinol 100 | EtOH 50 | 1 3 | 650 | 7 | 8% 4,4-di-(4-chlorophenyl)-but-3-enoic acid <br> 63% ethyl 4,4-di-(4-chlorophenyl)-but-3-enoate, bp. 208–212° C./4 mbar <br> 71% |
| 43 | Bis-(4-fluorophenyl)-vinylcarbinol 115 | EtOH 30 | 1 3 | 650 | 6 | 5% 4,4-di-(4-fluorophenyl)-but-3-enoic acid <br> 68% ethyl 4,4-di-(4-fluorophenyl)-but-3-enoate, bp. 148–153° C./4 mbar <br> 73% |
| 44 | 1-Vinyl-2,3-6,7-dibenzo-cyclohept-4-en-1-ol 105 | EtOH 50 | 1 3 | 650 | 8 | 4% 3-(2,3-6,7-dibenzo-cyclohept-4-en-1-ylidene)-propionic acid <br> 69% ethyl 3-(2,3-6,7-dibenzo-cyclohept-4-en-1-ylidene)-propionate, bp. 168–170° C./4 mbar <br> 73% |
| 45 | 1-Vinyl-2,3-6,7-dibenzo-cycloheptan-1-ol 100 | EtOH 50 | 1 3 | 650 | 6 | 3% 3-(2,3-6,7-dibenzocyclohept-1-ylidene-propionic acid <br> 69% ethyl 3-(2,3-6,7-dibenzocyclohept-1-ylidene-propionate, bp. 182–185° C./4 mbar <br> 72% |
| 46 | 3-(2-Methoxyphenyl)-prop-1-en-3-ol 103 | EtOH 50 | 1 3 | 650 | 12 | 8% 4-(2-methoxyphenyl)-but-3-enoic acid <br> 59% ethyl 4-(2-methoxyphenyl)-but-3-enoate, bp. 146–153° C./7 mbar <br> 67% |
| 47 | 3,7-Dimethyl-octa-1,6-dien-3-ol 1,000 | tert.-ButOH 500 | 2.5 7.5 | 300 | 9 | 66% 4,8-dimethyl-nona-3,7-dienoic acid <br> 20% tert.-butyl 4,8-dimethyl-nona-3,7-dienoate, bp. 97–98° C./6 mbar <br> 86% |
| 48 | 3,7-Dimethyl-oct-1-en-3-ol 1,000 | tert.-ButOH 500 | 2.5 7.5 | 300 | 13 | 64% 4,8-dimethyl-non-3-enoic acid, <br> 18% tert.-butyl 4,8-dimethyl-non-3-enoate, bp. 88° C./4 mbar <br> 82% |
| 49 | 3-Methyl-but-1-en-3-ol 1,000 | tert.-ButOH 500 | 2.5 7.5 | 300 | 22 | 71% 4-methyl-but-3-enoic acid <br> 13% tert.-butyl 4-methyl-but-3-enoate, bp. 87° C./48 mbar <br> 84% |
| 50 | 3-Methyl-but-1-en-3-ol 1,000 | tert.-ButOH 500 | 2.5 7.5** | 300 | 41 | 58% 4-methyl-but-3-enoic acid <br> 15% tert.-butyl 4-methyl-but-3-enoate, bp. 87° C./48 mbar <br> 73% |
| 51 | Oct-1-en-3-ol 1,000 | tert.-ButOH 500 | 2.5 7.5 | 300 | 32 | 63% oct-3-enoic acid <br> 12% tert.-butyl oct-3-enoate, bp. 72° C./6 mbar <br> 75% |
| 52 | 3,7,11-Trimethyl-dodeca-1,6,10-trien-3-ol (nerolidol) 1,000 | tert.-ButOH 500 | 2.5 7.5 | 300 | 32 | 74% 4,8,12-trimethyl-trideca-3,7,11-trienoic acid <br> 3% tert.-butyl 4,8,12-trimethyl-trideca-3,7,11-trienoate <br> 77% isomer mixture |
| 53 | 3,7,11-Trimethyl-dodeca-1,6,10-trien-3-ol (nerolidol) 1,000 | tert.-ButOH 500 | 2.5 15** | 300 | 28 | 82% 4,8,12-trimethyl-trideca-3,7,11-trienoic acid <br> 2% tert.-butyl 4,8,12-trimethyl-trideca-3,7,11-trienoate <br> 84% isomer mixture |
| 54 | 3,7,11,15-Tetramethyl-hexadec-1-en-3-ol (isophytol) 490 | tert.-ButOH 500 | 2.5 7.5 | 300 | 8 | 72% 4,8,12,16-tetramethyl-heptadec-3-enoic acid <br> 7% tert.-butyl 4,8,12,16-tetramethyl-heptadec-3-enoate, <br> 79% isomer mixture |
| 55 | Oct-1-en-3-ol 1,210 | — | 2.5 7.5 | 280 | 15 | 84% non-3-enoic acid, bp. 93–94° C./4 mbar q = 85:15 |
| 56 | 3,7-Dimethyl-octa-1,6-dien-3-ol (linalool) 1,500 | — | 2.5 7.5 | 280 | 16 | 83% 4,8-dimethyl-nona-3,7-dienoic acid, bp. 120–124° C./4 mbar q = 82:18 |
| 57 | 3-Methyl-but-1-en-3-ol 1,500 | — | 2.5 7.5 | 240 *** | 16 | 83% 4-methyl-but-3-enoic acid, bp. 70–71° C./4 mbar |
| 58 | 3,7,11-Trimethyl-dodeca-1,6,10-trien-3-ol 560 | — | 2.5 7.5 | 240 | 22 | 70% trimethyl-trideca-3,7,11-trienoic acid, bp. 165–170° C./1 mbar |

*Individual yields not determined
**n-Hexyldiphenylphosphine
***Temperature 80° C.

We claim:

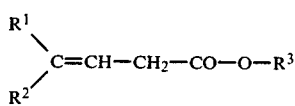

$$\text{(I)}$$

where $R^1$ is an organic radical, $R^2$ is hydrogen or an organic radical, and $R^1$ and $R^2$ may furthermore be bonded to one another to form a 5-membered to 20-membered ring and should be inert under the reaction conditions described below, and $R^3$ is hydrogen or lower alkyl, by carbonylation of a derivative of allyl alcohol with the aid of a palladium halide, wherein an allyl alcohol II

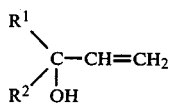

$$\text{(II)}$$

is carbonylated with carbon monoxide at 50°–150° C. and under 200–700 bar, (a) together with an alcohol III $$R^{3'}-OH \qquad \text{(III)}$$

where $R^{3'}$ is lower alkyl, if a predominant amount of an ester I is to be prepared, or (b) without a further reactant where an acid I is to be prepared, in the presence of an effective amount of complex of a palladium halide and a tertiary phosphine (IV).

2. A process as claimed in claim 1, wherein the carbonylation with carbon monoxide is carried out at a temperature of 90° to 110° C. and under a pressure of 300 to 600 bar.

3. A process as claimed in claim 1, wherein the molar ratio of phosphine to palladium is from 3:1 to 10:1.

4. A process as claimed in claim 1, wherein the amount of palladium is from 0.1 to 5 g per mole of the allyl alcohol II.

5. A process as claimed in claim 4, wherein the molar ratio of phosphine to palladium is from 3:1 to 10:1.

6. A process as claimed in claim 1, wherein the molar ratio of the alcohol III to the allyl alcohol II is from 2:1 to 6:1.

* * * * *

UNITED STATES PATENT AND TRADEMARK OFFICE
CERTIFICATE OF CORRECTION

PATENT NO. : 4,585,594
DATED      : April 29, 1986
INVENTOR(S) : Walter Himmele, Werner Hoffmann, Lothar Janitschke It is certified that error appears in the above-identified patent and that said Letters Patent is hereby corrected as shown below:

IN THE CLAIMS:

Please add the lines missing from the first claim directly preceeding the formula (I):

--1. A process for the preparation of a 4-substituted but-3-ene-1-carboxylic acid or its esters of the formula I --.

Column 12, Claim 1, line 9, before "complex", insert -- a --.

Signed and Sealed this

Fifth Day of August 1986

[SEAL]

Attest:

DONALD J. QUIGG

Attesting Officer

Commissioner of Patents and Trademarks